US006665888B1

(12) United States Patent
Kwak (10) Patent No.: US 6,665,888 B1
(45) Date of Patent: Dec. 23, 2003

(54) PORTABLE COLON IRRIGATOR

(76) Inventor: Hughes H. Kwak, 3994 S. 300 W. Suite 26, Salt Lake City, UT (US) 84107

(*) Notice: Subject to any disclaimer, the term of this patent is extended or adjusted under 35 U.S.C. 154(b) by 0 days.

(21) Appl. No.: 10/290,783

(22) Filed: Nov. 12, 2002

(51) Int. Cl.⁷ ................................................. E03D 9/08
(52) U.S. Cl. ...................... 4/420.1; 4/420.4; 604/185
(58) Field of Search ............................. 4/420.1, 420.4, 4/448; 604/132, 153, 185, 257, 279

(56) References Cited

U.S. PATENT DOCUMENTS

| 43,158 A | * | 6/1864 | Shepard ...................... 604/185 |
| 429,374 A | | 6/1890 | Charlesworth ................. 4/444 |
| 788,176 A | * | 4/1905 | Traves ......................... 604/185 |
| 1,838,356 A | | 12/1931 | Berry ....................... 4/420.1 X |
| 1,992,132 A | | 2/1935 | Spicher .................... 4/420.1 X |
| 2,044,911 A | * | 6/1936 | Miller ......................... 604/185 |
| 2,058,003 A | | 10/1936 | Davies ..................... 4/420.1 X |
| 2,528,095 A | | 10/1950 | Ward ....................... 4/420.1 X |
| 2,705,495 A | | 4/1955 | Vrana et al. .............. 4/420.1 X |
| 3,164,846 A | | 1/1965 | Foster ............................. 4/448 |
| 3,288,140 A | | 11/1966 | McCarthy ................. 4/420.1 X |
| 3,808,608 A | | 5/1974 | Caplan ........................... 4/448 |
| 4,696,673 A | | 9/1987 | Ledin-Bonevik ............ 604/150 |
| 5,380,275 A | * | 1/1995 | Kensey et al. ............ 4/420.1 X |

* cited by examiner

Primary Examiner—Robert M. Fetsuga
(74) Attorney, Agent, or Firm—Park & Sutton LLP; John K. Park (57) ABSTRACT

A portable colon irrigator is provided. The colon irrigator includes a manually operated pump, a first hose connecting the manually operated pump and a water source, a water ejector having an ejector body and an irrigating nozzle attached to the ejector body for being inserted into the anus of a user, a second hose connecting the manually operated pump and the ejector body, and two wings attached to the ejector body. The manually operated pump provides pressure to eject water from the irrigating nozzle and prevents backflow from the second hose, and the wings rest on a toilet. The colon irrigator may further include a branching valve and spraying nozzles so that it may also used as a bidet.

20 Claims, 7 Drawing Sheets

PORTABLE COLON IRRIGATOR

BACKGROUND OF THE INVENTION

The present invention relates to a colon irrigator. More particularly, the invention relates to a portable irrigator that can easily installed on and removed from a toilet.

There are many implementations of a colon irrigator by prior art. U.S. Pat. No. 429,374 discloses a syringe-type water ejector to clean colon over a toilet-bowl-like apparatus. U.S. Pat. No. 1,838,356 discloses a colon irrigator that can be fixed to a seat of a toilet with bolts and nuts. U.S. Pat. No. 1,992,132 discloses a colon irrigator having a clamp, a swivel member and a rigid tube. U.S. Pat. No. 2,058,003 discloses a colon irrigator having an irrigating nozzle adapted to be fixed to a toilet and a mixing device having two-way input of hot and cold water. U.S. Pat. No. 2,528,095 discloses a syringe nozzle holder that has a wire arrangement adapted to hold a tubing. U.S. Pat. No. 2,705,495 discloses a fountain syringe that has clips to fix the syringe to a toilet and a height adjuster for the syringe. U.S. Pat. No. 3,164,846 discloses a portable bidet having a nozzle, a hose and two plates. The plates have slots for attaching the nozzle. The overlapping distance of the plates is adjustable to put the bidet on a toilet. U.S. Pat. No. 3,288,140 discloses a device for treating a wound that has wires to position the device on a toilet. U.S. Pat. No. 3,808,608 discloses a portable bidet having a nozzle, a clamp to fix the nozzle to a toilet, a tube, a powered pump and a water reservoir. U.S. Pat. No. 4,696,673 discloses a colon irrigator that uses spring wires to attach a nozzle to a toilet basin.

The prior art devices are bulky, heavy and not handy to install and remove. Also the prior art devices do not have a control means that can adjust the water flow rate precisely.

SUMMARY OF THE INVENTION

The present invention contrives to solve the disadvantages of prior art.

Therefore, an object of the invention is to provide a small, light and handy colon irrigator.

Another object of the invention is to provide a colon irrigator that can adjust the water flow rate precisely.

Still another object of the invention is to provide a colon irrigator that has the functionality of a bidet also.

To achieve the above-described objects, the present invention provides a portable colon irrigator. The colon irrigator comprises a manually operated pump, a first hose connecting the manually operated pump and a water source, a water ejector having an ejector body and an irrigating nozzle attached to the ejector body for being inserted into the anus of a user, a second hose connecting the manually operated pump and the ejector body, and one or more wings attached to the ejector body. The manually operated pump provides pressure to eject water from the irrigating nozzle and prevents backflow from the second hose, and the wings rest on a toilet.

The wing comprises a wire having a shape of rotated "U", and the wire has two ends that are attached to the ejector body. The wire has bent portions near the ends to position the ejector body lower than a seat of the toilet. A water tank may be used as the water source. The ejector body includes a first cavity that guides water flow from the second hose to the irrigating nozzle.

The water ejector may further include one or more spraying nozzles, and the ejector body may further have a second cavity that guides water flow to the spraying nozzles.

A branching valve may be provided between the second hose and the ejector body. The branching valve includes a valve body and a selector. The valve body includes a circular chamber, a flow-in conduit connected to the chamber, a first flow-out conduit connected to the chamber, and a second flow-out conduit connected the chamber. The selector guides water flow from the flow-in conduit to the first or second flow-out conduits.

The selector has a shape of cylinder and is rotationally received in the chamber of the valve body.

The selector has a selector cavity, a first hole, a second hole, a third hole and a fourth hole. The first hole, the second hole and the third hole are provided near one end of the selector cavity. The fourth hole is provided near the other end of the selector cavity. The first hole is positioned perpendicular with the second hole, and the second hole is positioned perpendicular with the third hole. The fourth hole is parallel with the second hole. When the first hole is aligned with the flow-in conduit, the third hole is aligned with the first flow-out conduit, and the second hole and the fourth hole are blocked by the wall of the chamber so that water flows out through the first flow-out conduit. When the second hole is aligned with the flow-in conduit, the fourth hole is aligned with the second flow-out conduit, and the first hole and the third hole are blocked by the wall of the chamber so that water flows out through the second flow-out conduit.

The valve body has a rectangular recess. The selector further has a handle for rotating the selector, and a projection in the manner that the projection moves in the rectangular recess when the selector is rotated such that rotation of the selector is limited up to 90 degrees.

A third hose and a fourth hose are provided to connect the first and second flow-out conduits of the branching valve and the ejector body.

The manually operated pump includes an elastic tube, a top check valve that is installed at the upstream end of the elastic tube, and a bottom check valve that is installed at the downstream end of the elastic tube. The top and bottom check valves prevent reverse water flow.

The top check valve has a ball and a stop portion that limits the upstream movement of the ball, and a bottom holding sleeve that limits the downstream movement of the ball. The top stop portion has a circular cross section and the bottom holding sleeve has a circular cross section and one or more channels along the cross section so that when the ball contacts with the top stop portion, water flow is blocked, and when the ball contacts with the bottom holding sleeve, water can flow through the channels.

The bottom check valve has a ball and a top holding sleeve that limits the upstream movement of the ball, and a bottom stop portion that limits the downstream movement of the ball. The top holding sleeve has a circular cross section and the bottom stop portion has a circular cross section and one or more channels along the cross section so that when the ball contacts with the top holding sleeve, water flow is blocked, and when the ball contacts with the bottom stop portion, water can flow through the channels.

The advantages of the present invention are numerous in that: (1) a light, small and portable colon irrigator is provided; (2) a user can adjust the water flow rate as delicate as she or he wants; and (3) the user can also clean her or his skin after colon irrigation.

Although the present invention is briefly summarized, the fuller understanding of the invention can be obtained by the following drawings, detailed description and appended claims.

BRIEF DESCRIPTION OF THE DRAWINGS

These and other features, aspects and advantages of the present invention will become better understood with reference to the accompanying drawings, wherein.

DETAILED DESCRIPTION OF THE PREFERRED EMBODIMENTS

Figure 1:
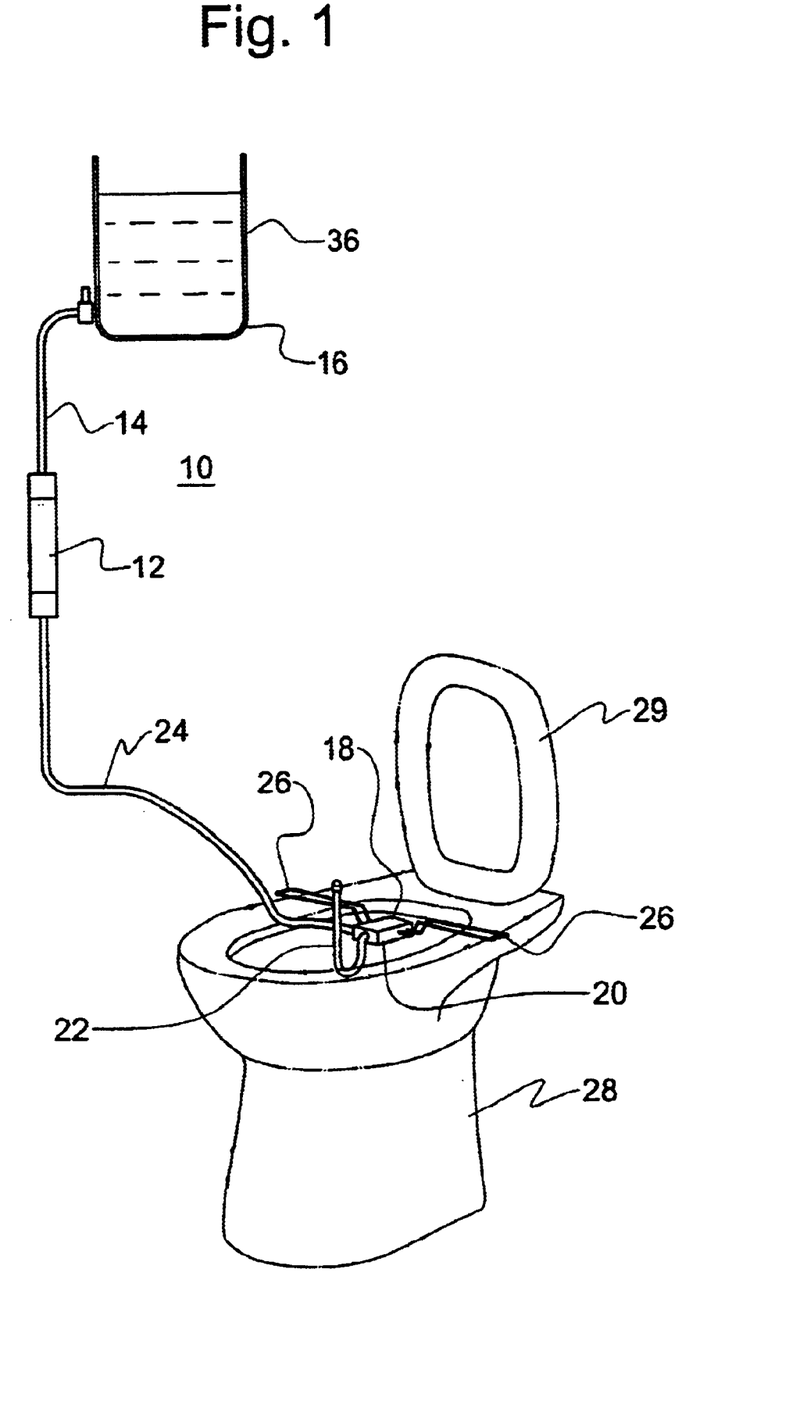
FIG. 1 is a schematic view showing a portable colon irrigator of the present invention.

FIG. 1 shows a portable colon irrigator 10 of the present invention. The colon irrigator 10 comprises a manually operated pump 12, a first hose 14 connecting the manually operated pump 12 and a water source 16, a water ejector 18 having an ejector body 20 and an irrigating nozzle 22 attached to the ejector body 20 for being inserted into the anus of a user, a second hose 24 connecting the manually operated pump 12 and the ejector body 20, and one or more wings 26 attached to the ejector body 20. The manually operated pump 12 provides pressure to eject water from the irrigating nozzle 22 and prevents backflow from the second hose 24. The wings 26 rest on a toilet 28 to position the water ejector 18 for colon irrigation. A toilet seat 29 of the toilet 28 is put on the wings 26 to secure the colon irrigator 10 to the toilet 28. FIG. 1 shows the state that the wings 26 are put on the toilet 28 and the toilet seat 29 is about to be pivoted down.

Figure 2:
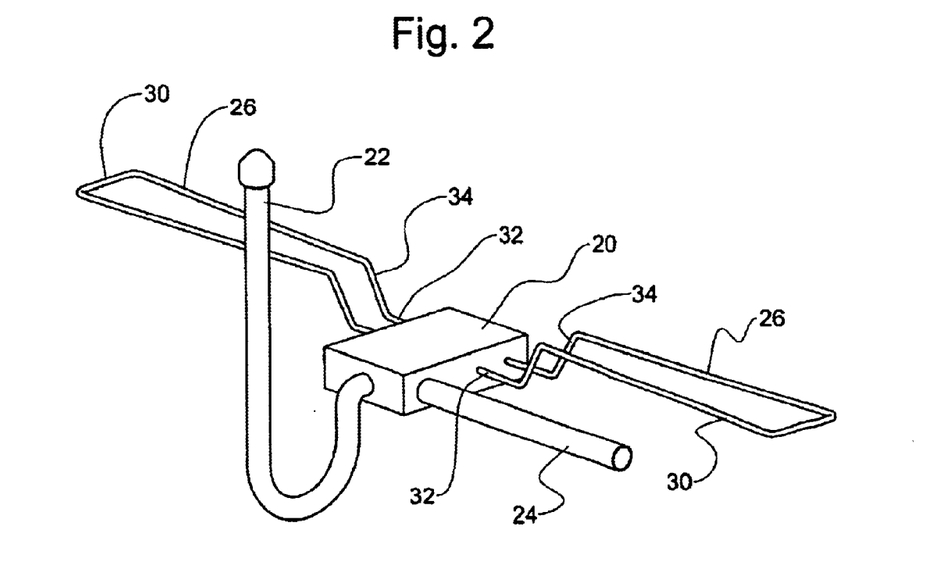
FIG. 2 is a perspective view of a water ejector together with wings.
Figure 3:
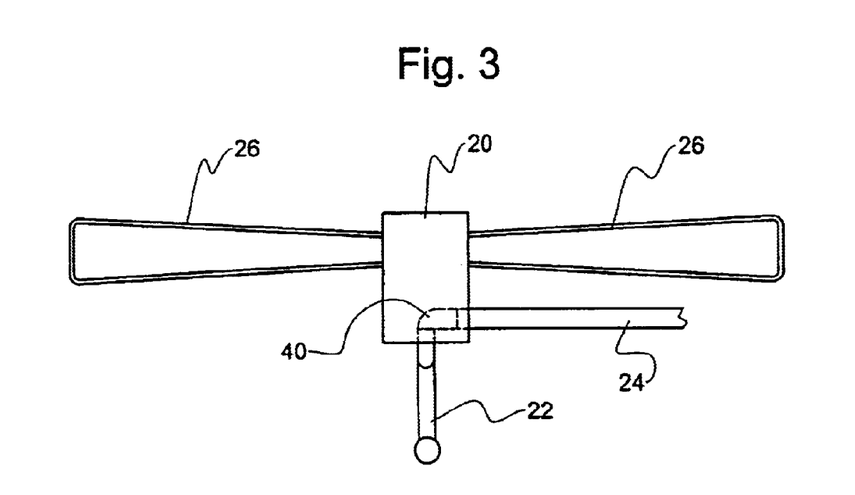
FIG. 3 is a plan view of the water ejector.

FIGS. 2 and 3 show that the wing 26 comprises a wire 30 having a shape of rotated "U", and the wire 30 has two ends 32 that are attached to ejector body 20. Each of the wires 30 has bent portions 34 near the ends 32 to position the ejector body 20 lower than a seat of the toilet 28. Installing the colon irrigator 10 on the toilet 28 simply requires putting the wires 30 on the toilet 28 and pivoting down the toilet seat 29. The colon irrigator 10 consists of small and light parts, and thus is quite portable and easy to store and carry.

The water source 16 may be a water tank 36 as shown in FIG. 1. Water or a cleaning liquid containing substances suitable for colon irrigation may be filled in the water tank 36.

FIG. 3 shows that the ejector body 20 includes a first cavity 40 that guides water flow from the second hose 24 to the irrigating nozzle 22. The ejector body 20 may be molded with plastic materials.

Figure 4:
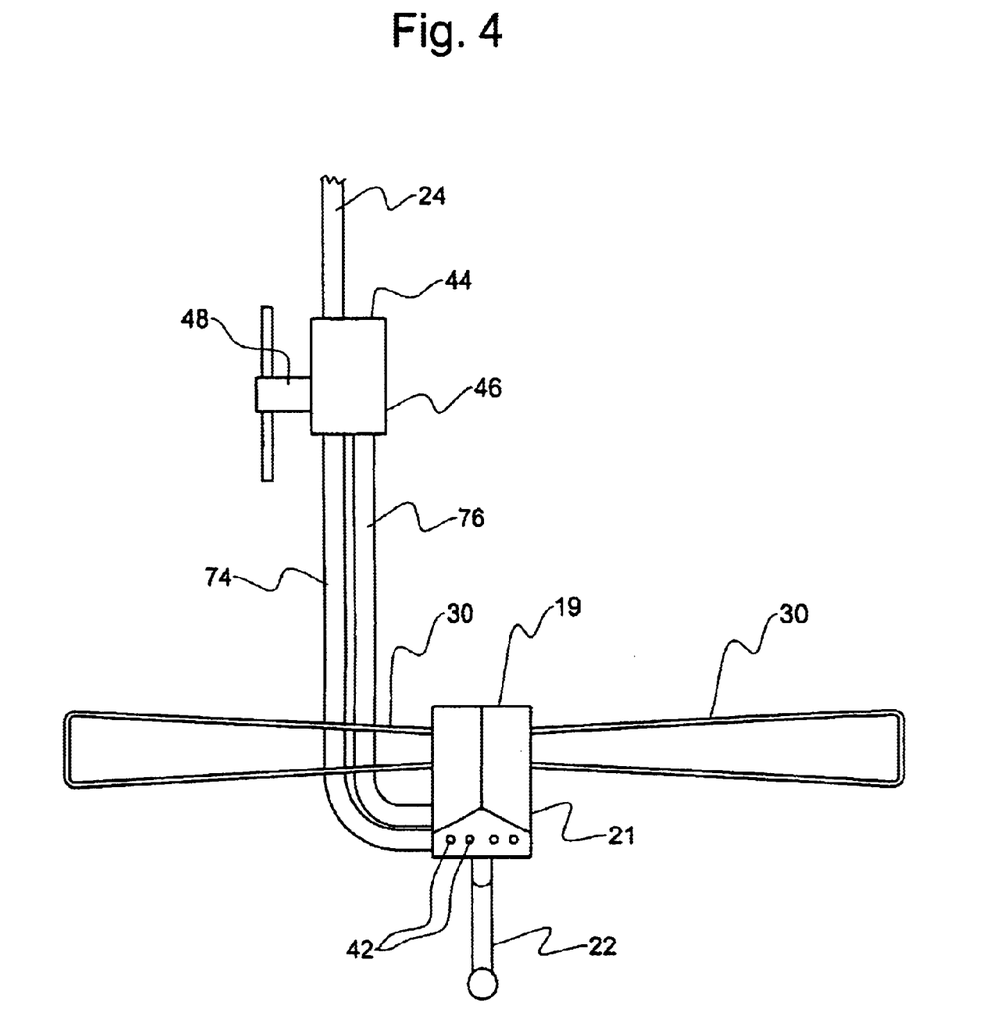
FIG. 4 is a perspective view showing another water ejector having an irrigating nozzle and a plurality if spraying nozzles, and a branching valve.
Figure 5:
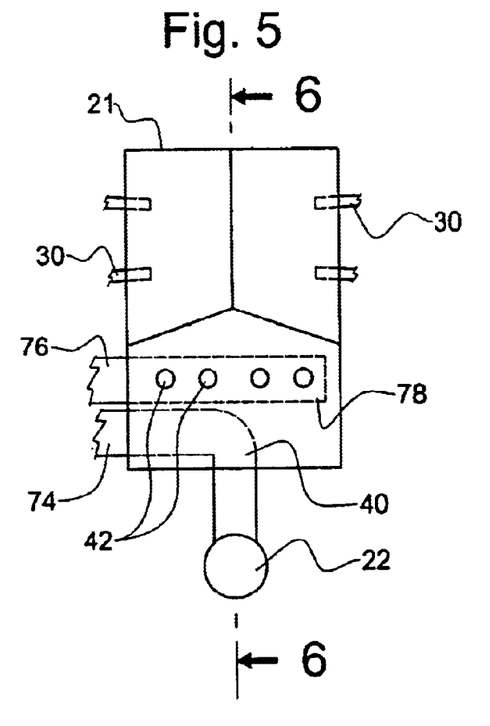
FIG. 5 is an illustrative view of the water ejector.
Figure 6:
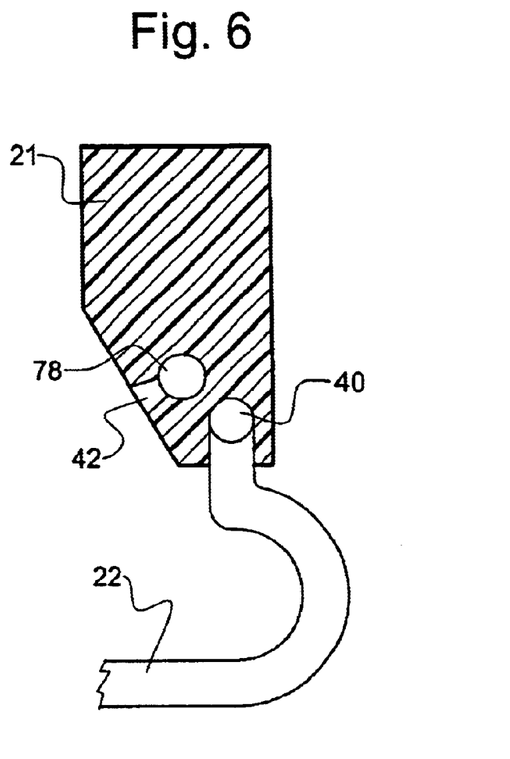
FIG. 6 is a cross-sectional view taken along the line 6—6 in FIG. 5.

FIGS. 4, 5 and 6 show another embodiment of a water ejector 19. The water ejector 19 is similar to the water ejector 18 but further includes one or more spraying nozzles 42. The spraying nozzles 42 are provided in an ejector body 21 of the water ejector 19.

The spraying nozzles 42 are used to eject water to clean the skin around the anus of a user. The user may direct water through the irrigating nozzle 22 or the spraying nozzles 42 with a branching valve 44 that is explained below.

Figure 7:
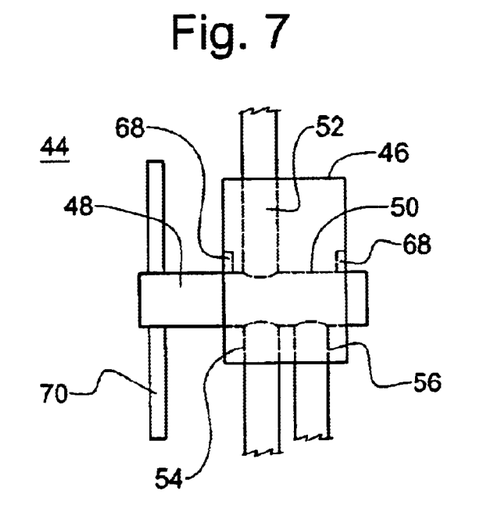
FIG. 7 is a plan view of the branching valve.
Figure 8:
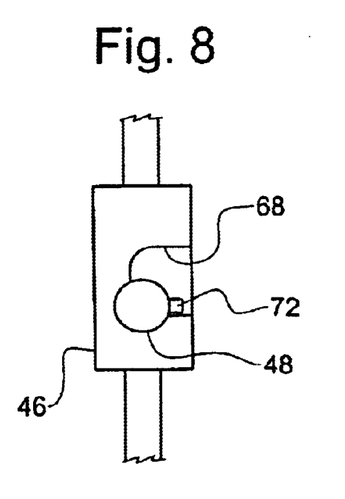
FIG. 8 is a side elevation view of the branching valve.

FIGS. 4, 7 and 8 show the branching valve 44 that is installed between the second hose 24 and the ejector body 21. As shown in FIG. 7, the branching valve 44 includes a valve body 46 and a selector 48. The body 48 includes a circular chamber 50, a flow-in conduit 52 connected to the chamber 50, a first flow-out conduit 54 connected to the chamber 50, and a second flow-out conduit 56 connected the chamber 50. The selector 48 guides water flow from the flow-in conduit 52 to the first flow-out conduit 54 or the second flow-out conduits 56.

Figure 9:
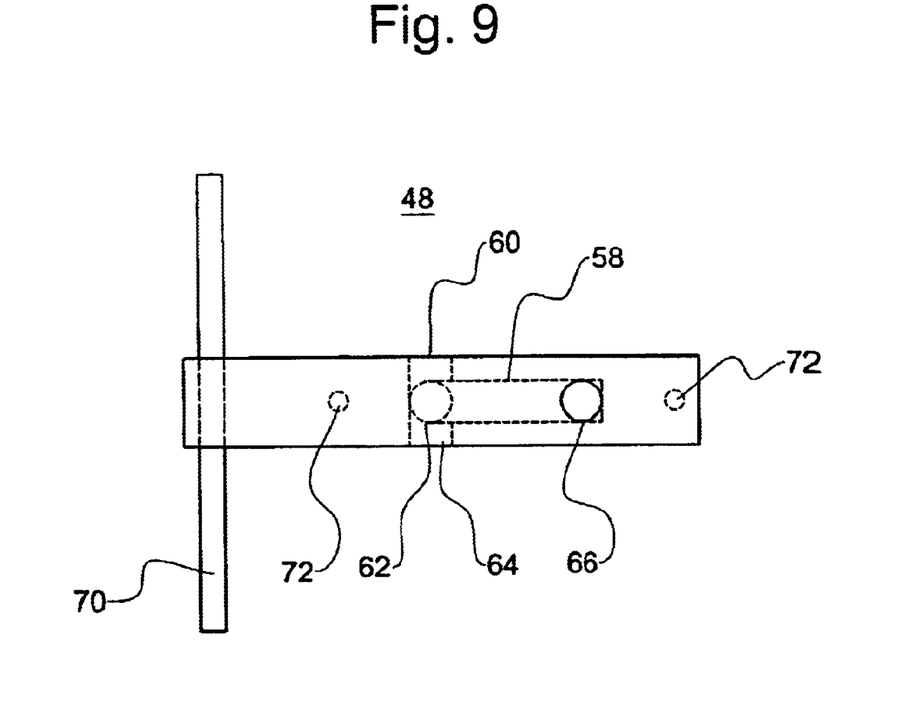
FIG. 9 is a plan view of a selector of the branching valve.
Figure 10:
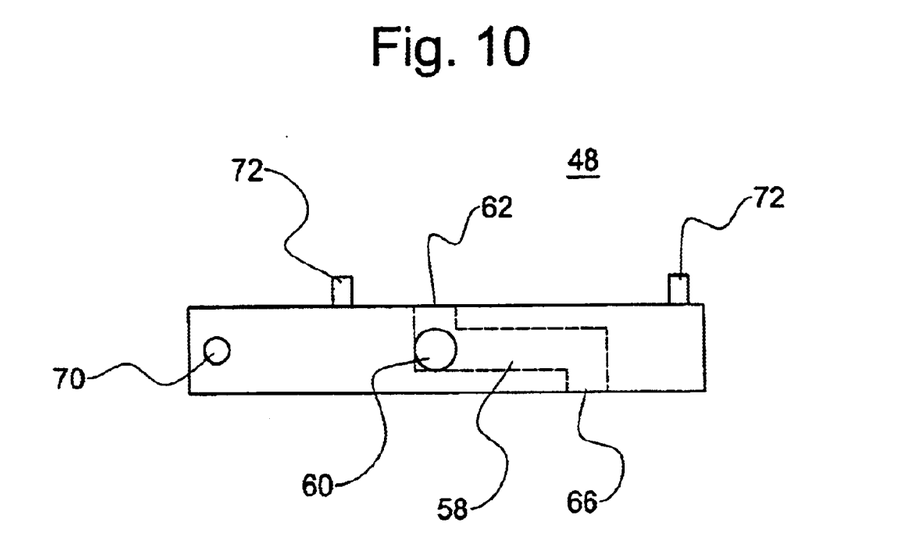
FIG. 10 is a front elevation view of the selector.

FIGS. 9 and 10 show the selector 48. The selector 48 has a shape of cylinder and is rotationally received in the chamber 50. The selector 48 has a selector cavity 58, a first hole 60, a second hole 62, a third hole 64 and a fourth hole 66. The first hole 60, the second hole 62 and the third hole 64 are provided near one end of the selector cavity 58. The fourth hole 66 is provided near the other end of the selector cavity 58. The first hole 60 is positioned perpendicular with the second hole 62, and the second hole 62 is positioned perpendicular with the third hole 64. The fourth hole 66 is parallel with the second hole 62. With this arrangement, when the first hole 60 is aligned with the flow-in conduit 52, the third hole 64 is aligned with the first flow-out conduit 54, and the second hole 62 and the fourth hole 66 are blocked by the wall of the chamber 50. Thus, water flows out through the first flow-out conduit 54. When the second hole 62 is aligned with the flow-in conduit 52 by rotating the selector 48 by 90 degrees, the fourth hole 66 is aligned with the second flow-out conduit 56, and the first hole 60 and the third hole 64 are blocked by the wall of the chamber 50. Thus, water flows out through the second flow-out conduit 56.

Referring back to FIGS. 7 and 8, the valve body 46 has one or more rectangular recess 68. The selector 48 includes a handle 70 for rotating the selector 48. The selector 48 has one or more projection 72 in the manner that the projection 72 move in the rectangular recesses 68 when the selector 48 is rotated such that rotation of the selector 48 is limited up to 90 degrees.

Referring back to FIG. 4, a third hose 74 and a fourth hose 76 connect the two flow-out conduits 54, 56 of the branching valve 44 and the ejector body 21 of the water ejector 19.

Referring back to FIGS. 5 and 6, the first cavity 40 of the ejector body 21 guides water flow from the third hose 74 to the irrigating nozzle 22. The ejector body 21 further includes a second cavity 78 that guides water flow from the fourth hose 76 to the spraying nozzles 42.

Figure 11:
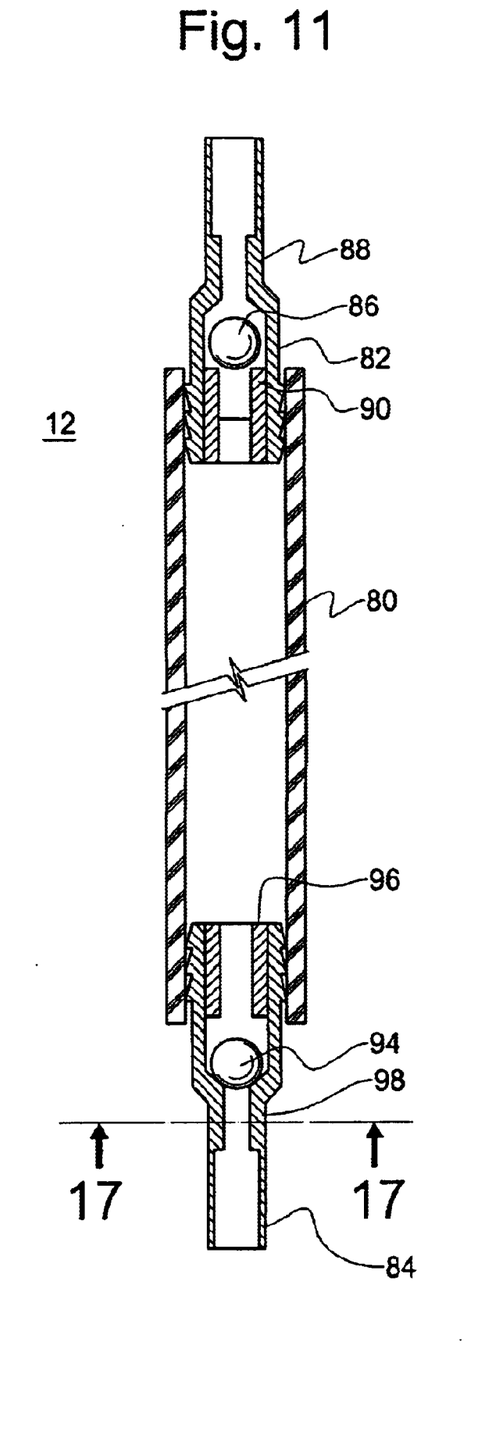
FIG. 11 is a cross-sectional view of a manually operated pump.
Figure 12:
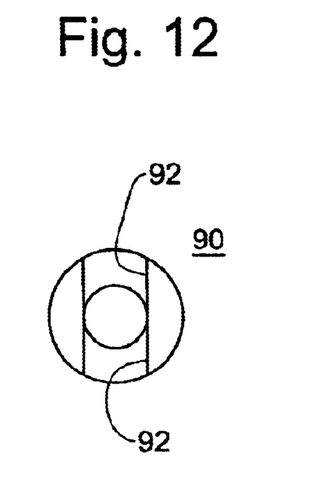
FIG. 12 is a plan view of a bottom holding sleeve.
Figure 13:
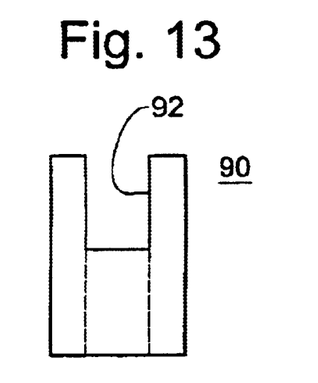
FIG. 13 is an elevation view of the bottom holding sleeve.
Figure 14:
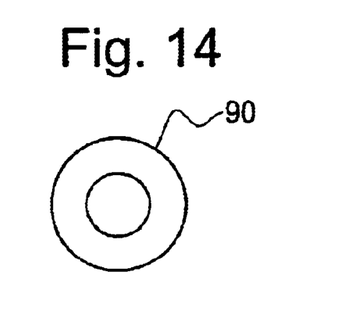
FIG. 14 is a bottom view of the bottom holding sleeve.
Figure 15:
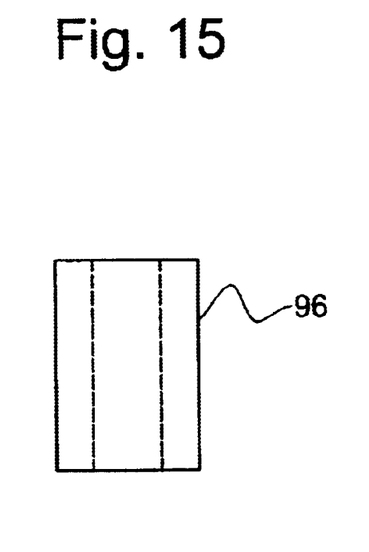
FIG. 15 is an elevation view of the top holding sleeve.
Figure 16:
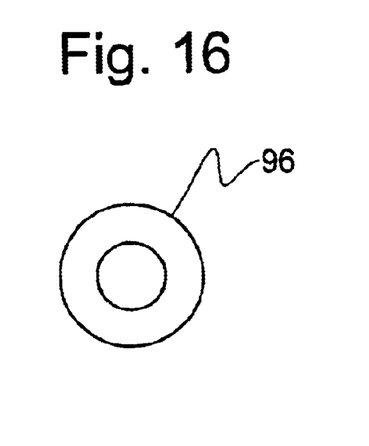
FIG. 16 is a bottom view of the top holding sleeve.
Figure 17:
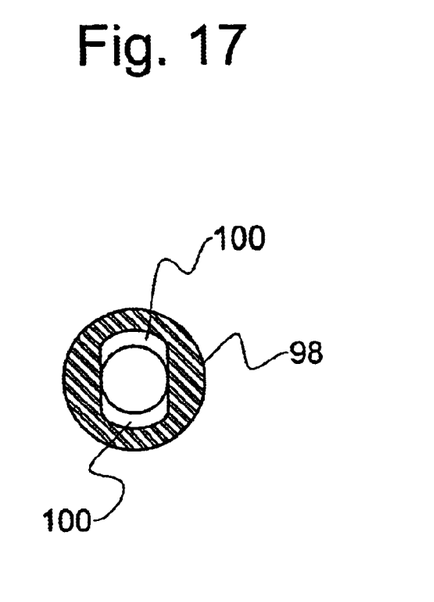
FIG. 17 is a cross-sectional view taken along the line 17—17 in FIG. 11.

FIG. 11 shows the manually operated pump 12. The manually operated pump 12 includes an elastic tube 80, a top check valve 82 that is installed at the upstream end of the elastic tube 80, and a bottom check valve 84 that is installed at the downstream end of the elastic tube 80. The top and bottom check valves 82, 84 prevent reverse water flow so that contaminants produced by colon irrigation do not get into the manually operated pump 12.

The top check valve 82 has a ball 86 and a top stop portion 88 that limits the upstream movement of the ball 86, and a bottom holding sleeve 90 that limits the downstream movement of the ball 86. The top stop portion 88 has a circular cross section and the bottom holding sleeve 90 has a circular cross section and one or more channels 92 along the cross section so that when the ball 86 contacts with the top stop portion 88, water flow is blocked, and when the ball 86 contacts with the bottom holding sleeve 90, water can flow through the channels 92 (refer to FIGS. 11–14). The bottom check valve 84 has a ball 94 and a top holding sleeve 96 that limits the upstream movement of the ball 94, and a bottom stop portion 98 that limits the downstream movement of the ball 94. The top holding sleeve 96 has a circular cross section and the bottom stop portion 98 has a circular cross section and one or more channels 100 along the cross section so that when the ball 94 contacts with the top holding sleeve 96, water flow is blocked, and when the ball 94 contacts with the bottom stop portion 98, water can flow through the channels 100 (refer to FIGS. 11 and 15–17).

The user squeezes the elastic tube 80 to eject water via the water ejector 18, 19. When the elastic tube 80 is squeezed, the ball 86 of the top check valve 82 contacts the top stop portion 88 and water cannot flow in reverse direction. On the other hand, the ball 94 of the bottom check valve 84 contacts bottom stop portion 98 and water flows out through the channels 100 of the bottom stop portion 98.

The user releases the elastic tube 80 to fill the elastic tube 80 with water. When the elastic tube 80 is released, the ball 86 of the top check valve 82 contacts the bottom holding sleeve 90 and water flows in through the channels 92 of the bottom holding sleeve 90. On the other hand, the ball 94 of the bottom check valve 84 contacts the top holding sleeve 96 and water cannot penetrate into the elastic tube 80.

The user can precisely adjust the pressure of the ejected water through the irrigating nozzle 22 or the spraying nozzles 42 by adjusting the force squeezing the elastic tube 80.

After finishing colon irrigation, the user can wash her or his skin around the anus by changing the water flow path with the branching valve 44.

With the above construction, a colon irrigator that is portable and easy to install and remove on a toilet is provided. The water ejection pressure can be controlled very precisely with the manually operated pump. The irrigator can be converted to a bidet by simply rotating the handle of the branching valve.

Although the invention has been described in considerable detail, other versions are possible by converting the aforementioned construction. Therefore, the scope of the invention shall not be limited by the specification specified above.

What is claimed is:

1. A portable colon irrigator comprising:
   a) a manually operated pump;
   b) a first hose connecting the manually operated pump and a water source;
   c) a water ejector having an ejector body and an irrigating nozzle attached to the ejector body for being inserted into the anus of a user;
   d) a second hose connecting the manually operated pump and the ejector body; and
   e) one or more wings attached to the ejector body; wherein the manually operated pump provides pressure to eject water from the irrigating nozzle and prevents backflow from the second hose, and wherein the wings rest on a toilet.

2. The portable colon irrigator of claim 1, wherein each of the wings comprise a wire having a shape of rotated "U", and wherein the wire has two ends that are attached to the ejector body.

3. The portable colon irrigator of claim 2, wherein the wire has bent portions near the ends to position the ejector body lower than a seat of the toilet.

4. The portable colon irrigator of claim 1, further comprising a water tank as the water source.

5. The portable colon irrigator of claim 1, wherein the ejector body further includes a first cavity that guides water flow from the second hose to the irrigating nozzle.

6. The portable colon irrigator of claim 1, wherein the water ejector further includes one or more spraying nozzles.

7. The portable colon irrigator of claim 6, further comprising a branching valve that is installed between the second hose and the ejector body, wherein the branching valve includes a valve body and a selector, wherein the valve body includes a circular chamber, a flow-in conduit connected to the chamber, a first flow-out conduit connected to the chamber, and a second flow-out conduit connected the chamber, wherein the selector guides water flow from the flow-in conduit to the first flow-out conduit or the second flow-out conduit.

8. The portable colon irrigator of claim 7, wherein the selector has a shape of cylinder and is rotationally received in the chamber, wherein the selector has a selector cavity, a first hole, a second hole, a third hole and a fourth hole, wherein the first hole, the second hole and the third hole are provided near one end of the selector cavity, wherein the fourth hole is provided near the other end of the selector cavity, wherein the first hole is positioned perpendicular with the second hole, and the second hole is positioned perpendicular with the third hole, wherein the fourth hole is parallel with the second hole, whereby when the first hole is aligned with the flow-in conduit, the third hole is aligned with the first flow-out conduit, and the second hole and the fourth hole are blocked by the wall of the chamber so that water flows out through the first flow-out conduit, whereby when the second hole is aligned with the flow-in conduit, the fourth hole is aligned with the second flow-out conduit, and the first hole and the third hole are blocked by the wall of the chamber so that water flows out through the second flow-out conduit.

9. The portable colon irrigator of claim 8, wherein the valve body has a rectangular recess, wherein the selector further has a handle for rotating the selector, and a projection in the manner that the projection moves in the rectangular recess when the selector is rotated such that rotation of the selector is limited up to 90 degrees.

10. The portable colon irrigator of claim 7, further comprising a third hose and a fourth hose, wherein the third hose and the fourth hose connect the first and second flow-out conduits of the branching valve and the ejector body.

11. The portable colon irrigator of claim 10, wherein the ejector body further includes a first cavity that guides water flow from the third hose to the irrigating nozzle, and a second cavity that guides water flow from the fourth hose to the spraying nozzles.

12. The portable colon irrigator of claim 11, wherein the manually operated pump includes an elastic tube, a top check valve that is installed at the upstream end of the elastic tube, and a bottom check valve that is installed at the downstream end of the elastic tube, and wherein the top and bottom check valves prevent reverse water flow.

13. The portable colon irrigator of claim 1, wherein the manually operated pump includes an elastic tube, a top check valve that is installed at the upstream end of the elastic tube, and a bottom check valve that is installed at the downstream end of the elastic tube, and wherein the top and bottom check valves prevent reverse water flow.

14. The portable colon irrigator of claim 13, wherein the top check valve has a ball and a stop portion that limits the upstream movement of the ball, and a bottom holding sleeve that limits the downstream movement of the ball, wherein the top stop portion has a circular cross section and the bottom holding sleeve has a circular cross section and one or more channels along the cross section so that when the ball contacts with the top stop portion, water flow is blocked, and when the ball contacts with the bottom holding sleeve, water can flow through the channels, wherein the bottom check valve has a ball and a top holding sleeve that limits the upstream movement of the ball, and a bottom stop portion that limits the downstream movement of the ball, wherein the top holding sleeve has a circular cross section and the bottom stop portion has a circular cross section and one or more channels along the cross section so that when the ball contacts with the top holding sleeve, water flow is blocked, and when the ball contacts with the bottom stop portion, water can flow through the channels.

15. The portable colon irrigator of claim 12, wherein the top check valve has a ball and a stop portion that limits the upstream movement of the ball, and a bottom holding sleeve that limits the downstream movement of the ball, wherein the top stop portion has a circular cross section and the bottom holding sleeve has a circular cross section and one or more channels along the cross section so that when the ball contacts with the top stop portion, water flow is blocked, and when the ball contacts with the bottom holding sleeve, water can flow through the channels, wherein the bottom check valve has a ball and a top holding sleeve that limits the upstream movement of the ball, and a bottom stop portion that limits the downstream movement of the ball, wherein the top holding sleeve has a circular cross section and the bottom stop portion has a circular cross section and one or more channels along the cross section so that when the ball contacts with the top holding sleeve, water flow is blocked, and when the ball contacts with the bottom stop portion, water can flow through the channels.

16. The portable colon irrigator of claim 15 wherein each of the wings comprise a wire having a shape of rotated "U", and wherein the wire has two ends that are attached to the ejector body.

17. The portable colon irrigator of claim 16, wherein the wire has bent portions near the ends to position the ejector body lower than a seat of the toilet.

18. The portable colon irrigator of claim 17, further comprising a water tank as the water source.

19. The portable colon irrigator of claim 18, wherein the selector has a shape of cylinder and is rotationally received in the chamber, wherein the selector has a selector cavity, a first hole, a second hole, a third hole and a fourth hole, wherein the first hole, the second hole and the third hole are provided near one end of the selector cavity, wherein the fourth hole is provided near the other end of the selector cavity, wherein the first hole is positioned perpendicular with the second hole, and the second hole is positioned perpendicular with the third hole, wherein the fourth hole is parallel with the second hole, whereby when the first hole is aligned with the flow-in conduit, the third hole is aligned with the first flow-out conduit, and the second hole and the fourth hole are blocked by the wall of the chamber so that water flows out through the first flow-out conduit, whereby when the second hole is aligned with the flow-in conduit, the fourth hole is aligned with the second flow-out conduit, and the first hole and the third hole are blocked by the wall of the chamber so that water flows out through the second flow-out conduit.

20. The portable colon irrigator of claim 19, wherein the valve body has a rectangular recess, wherein the selector further has a handle for rotating the selector, and a projection in the manner that the projection moves in the rectangular recess when the selector is rotated such that rotation of the selector is limited up to 90 degrees.

* * * * *